US012668618B2

(12) United States Patent
Li et al.

(10) Patent No.: US 12,668,618 B2
(45) Date of Patent: Jun. 30, 2026

(54) APPLICATION OF MmPI IN PREPARATION OF TRYPSIN INHIBITORS

(71) Applicant: SHAANXI UNIVERSITY OF TECHNOLOGY, Hanzhong (CN)

(72) Inventors: Youshan Li, Hanzhong (CN); Rui Zhu, Hanzhong (CN); Zhuxing Luo, Hanzhong (CN)

(73) Assignee: SHAANXI UNIVERSITY OF TECHNOLOGY, Hanzhong (CN)

( * ) Notice: Subject to any disclaimer, the term of this patent is extended or adjusted under 35 U.S.C. 154(b) by 325 days.

(21) Appl. No.: 18/536,520

(22) Filed: Dec. 12, 2023

(65) Prior Publication Data

US 2024/0150435 A1     May 9, 2024

Related U.S. Application Data

(63) Continuation of application No. PCT/CN2023/111382, filed on Aug. 7, 2023.

(30) Foreign Application Priority Data

Sep. 16, 2022    (CN) .......................... 202211127984.0

(51) Int. Cl.
 *C07K 14/81* (2006.01)
 *C12N 15/74* (2006.01)
(52) U.S. Cl.
 CPC ............ *C07K 14/811* (2013.01); *C12N 15/74* (2013.01)
(58) Field of Classification Search
 CPC ............................... C07K 14/811; C12N 15/74
 See application file for complete search history.

(56) References Cited

U.S. PATENT DOCUMENTS 10,342,764 B2 *   7/2019   Hershko .............. A61K 9/4858

OTHER PUBLICATIONS

UniProt No. P01055, https://www.uniprot.org/uniprotkb/P01055/entry#sequences (Year: 1996).*
GenBank: X68704.1, https://www.ncbi.nlm.nih.gov/nuccore/X68704 (Year: 1997).*
Avilés-Gaxiola S, Chuck-Hernández C, Serna Saldívar SO. Inactivation Methods of Trypsin Inhibitor in Legumes: A Review. J Food Sci. Jan. 2018;83(1):17-29. doi: 10.1111/1750-3841.13985. Epub Dec. 6, 2017. PMID: 29210451. (Year: 2018).*

* cited by examiner

*Primary Examiner* — Louise W Humphrey
*Assistant Examiner* — Rachel Emily Martin
(74) *Attorney, Agent, or Firm* — Hemisphere Law, PLLC

(57) ABSTRACT

The present disclosure relates to the field of genetic engineering or enzyme engineering, and in particular to an application of MmBBK2 in preparation of trypsin and chymotrypsin inhibitors. The MmBBK2 has the amino acid sequence shown in SEQ ID NO. 1 or SEQ ID NO. 2. The present disclosure clarifies for the first time that MmBBK2 in mulberry leaves has both trypsin and chymotrypsin inhibitory activity, and reveals its physical and chemical properties. The MmBBK2 has good application prospects in preparing trypsin and chymotrypsin inhibitors. On the basis of knowing its physical and chemical properties, its activity may be accordingly eliminated, promoting the development and utilization of mulberry leaf resources in animal feed, providing new perspectives and ideas for the development and utilization of mulberry leaves in animal feed and health food, and improving economic benefits of mulberry resources.

4 Claims, 11 Drawing Sheets

Specification includes a Sequence Listing.

SEQUENCE LISTING

```
Sequence total quantity: 9
SEQ ID NO: 1          moltype = AA  length = 122
FEATURE               Location/Qualifiers
source                1..122
                      mol_type = protein
                      organism = Morus alba
```

```
SEQUENCE: 1
MAFIKVSVLL LLLSEGFVAP IADARGNLFR VSNDAQSLGF GQKFCSTCEC ETESETTTCY    60
RTDRKIGGCP LVCGEPCICT RSIPPICFCR YEVETCNPEQ CNPIGTTDLM LTFEKLLAVK   120
GA                                                                  122

SEQ ID NO: 2            moltype = AA   length = 122
FEATURE                 Location/Qualifiers
source                  1..122
                        mol_type = protein
                        organism = Morus alba
SEQUENCE: 2
MAFIKVSVLL LLLFVVLVAP IADARGNLFR VSNDAQSLGF GQKFCSTCEC ETESETTTCY    60
RTDRKIGGCP LVCGEPCICT RSIPPICFCR YEVETCNPEQ CNSIGTTDHM LTFEKLLAVK   120
GA                                                                  122

SEQ ID NO: 3            moltype = DNA   length = 369
FEATURE                 Location/Qualifiers
source                  1..369
                        mol_type = genomic DNA
                        organism = Morus alba
SEQUENCE: 3
atggcattca tcaaagtttc tgttttgttg ttgctgctgt ccgaagggtt tgttgctcca    60
atagctgatg ctcggggaaa ccttttccgg gtttctaatg atgctcaatc tctaggtttt   120
ggacaaaaat tctgctctac ctgtgagtgc gagacagaat ccgaaaccac aacatgttat   180
cgtacggaca gaaagatagg cggatgcccc ttagtttgcg gagaaccttg catttgtaca   240
agaagtatcc caccaatatg cttttgcaga tatgaggttg agacctgcaa tcctgaacaa   300
tgcaacccca tcggcactac tgatcttatg ctgacgtttg agaaacttct cgctgtcaaa   360
ggcgcatga                                                           369

SEQ ID NO: 4            moltype = DNA   length = 369
FEATURE                 Location/Qualifiers
source                  1..369
                        mol_type = genomic DNA
                        organism = Morus alba
SEQUENCE: 4
atggcattca tcaaagtttc tgttttgttg ttgctgctgt ttgttgtgct tgttgctcca    60
atagctgatg ctcggggaaa ccttttccgg gtttctaatg atgctcaatc tctaggtttt   120
ggacaaaaat tctgctctac ctgtgagtgc gagacagaat ccgaaaccac aacatgttat   180
cgtacggaca gaaagatagg cggatgcccc ttagtttgcg gagaaccttg catttgtaca   240
agaagtatcc caccaatatg cttttgcaga tatgaggttg agacctgcaa tcctgaacaa   300
tgcaactcca tcggcactac tgatcatatg ctgacgtttg agaaacttct cgctgtcaaa   360
ggcgcatga                                                           369

SEQ ID NO: 5            moltype = DNA   length = 23
FEATURE                 Location/Qualifiers
source                  1..23
                        mol_type = other DNA
                        organism = synthetic construct
SEQUENCE: 5
atggcattca tcaaagtttc tgt                                            23

SEQ ID NO: 6            moltype = DNA   length = 18
FEATURE                 Location/Qualifiers
source                  1..18
                        mol_type = other DNA
                        organism = synthetic construct
SEQUENCE: 6
tcatgcgcct ttgacagc                                                 18

SEQ ID NO: 7            moltype = DNA   length = 27
FEATURE                 Location/Qualifiers
source                  1..27
                        mol_type = other DNA
                        organism = synthetic construct
SEQUENCE: 7
cgccatatgc ggggaaacct tttccgg                                       27

SEQ ID NO: 8            moltype = DNA   length = 27
FEATURE                 Location/Qualifiers
source                  1..27
                        mol_type = other DNA
                        organism = synthetic construct
SEQUENCE: 8
cgcattaatc ggggaaacct tttccgg                                       27

SEQ ID NO: 9            moltype = DNA   length = 31
FEATURE                 Location/Qualifiers
source                  1..31
                        mol_type = other DNA
```

-continued

--- organism = synthetic construct
SEQUENCE: 9
atttgcggcc gctcatgcgc ctttgacagc g                                    31

APPLICATION OF MmPI IN PREPARATION OF TRYPSIN INHIBITORS

TECHNICAL FIELD

The present disclosure relates to the field of genetic engineering or enzyme engineering, and in particular to an application of MmBBK2 in preparation of trypsin and chymotrypsin inhibitors.

BACKGROUND

As a new and high-quality animal feed additive, mulberry leaves can not only improve the animal growth performance and the quality of poultry and livestock products, but also avoid the waste of mulberry leaf resources and improve the comprehensive economic benefits of the sericulture industry. However, due to the presence of anti-nutritional factors such as tannins, protease inhibitors and lectins in mulberry leaves, large amounts of mulberry leaves consumed by animals will seriously interfere with their metabolism and absorption of feed nutrients, thereby affecting the health of livestock and poultry and the yield and quality of livestock and poultry products, and greatly limiting the development and application of mulberry leaf resources in animal feed. Serine protease inhibitor (SPI) is a kind of protease inhibitors that is the most numerous and most intensively studied, it includes trypsin inhibitor (TI), chymotrypsin inhibitor (CI), elastase inhibitor (EI) and subtilisin inhibitor (SI), etc.

Based on the active site, mechanism of action of SPI, and its distribution in plants, plant SPI can be divided into eight families/categories, among which the Kunitz, Serpin, Bowman-Birk, PI-I and PI-II families have been studied more intensively. A total of 79 protease inhibitors (PIs), including 35 SPIs that belong to the Kunitz, Serpin and PI-I families, were identified in the *Morus notabilis* genome. After analyzing the expression of different SPI family genes in various tissues, it was found that 8 Kunitz-family SPI genes and 1 Serpin-family SPI gene were mainly expressed in mulberry leaves. It is found by Western Blot detection that the serine protease inhibitor MmKPI-9 is expressed in mulberry leaves, but TI activity bands are not detected by in-gel activity staining. Wang Dandan used in-gel activity staining technology to detect multiple CI activity bands in the white latex flowing out of the petioles of mulberry leaves, but no CI activity was detected in the mulberry leaves. At present, there are few research reports on anti-nutritional factor SPIs in mulberry leaves, and the sequence information, activity, and physical and chemical properties of these SPIs are still unclear.

SUMMARY

In order to solve the above technical problems, the present disclosure provides an application of MmBBK2 in preparing trypsin and chymotrypsin inhibitors, wherein an amino acid sequence of the MmBBK2 is as shown in SEQ ID NO. 1 or SEQ ID NO. 2.

Based on the same inventive concept, the present disclosure also provides a gene encoding the MmBBK2, wherein a nucleotide sequence of an encoding gene with the amino acid sequence shown in SEQ ID NO. 1 is shown in SEQ ID NO. 3, and a nucleotide sequence of an encoding gene with the amino acid sequence shown in SEQ ID NO. 2 is shown in SEQ ID NO. 4.

Based on the same inventive concept, the present disclosure also provides a plasmid carrying the gene, obtained by connecting the encoding gene shown in SEQ ID NO. 3 or SEQ ID NO. 4 to a p28 expression vector, and connection sites of the encoding gene shown in SEQ ID NO. 3 are Nde I and Not I, and connection sites of the encoding gene shown in SEQ ID NO. 4 are Ase I and Not I.

Based on the same inventive concept, the present disclosure also provides a host expression strain carrying the plasmid, wherein the host expression strain is Origami 2 (DE3) strain.

Based on the same inventive concept, the present disclosure also provides a method of eliminating the activity of MmBBK2, comprising: placing the MmBBK2 in an environment with pH 3~4; or, placing the MmBBK2 in an environment of 121° C. and 0.21 MPa for 20 minutes; or, treating the MmBBK2 using a reducing agent β-mercaptoethanol at 100° C. for 10 minutes; or, eliminating MmBBK2 activity by Maillard reaction mediated by reducing sugar.

The disclosure has the following beneficial effects:

The present disclosure clarifies for the first time that MmBBK2 in mulberry leaves has both trypsin and chymotrypsin inhibitory activity, and reveals its physical and chemical properties. MmBBK2 has good application prospects in preparing trypsin and chymotrypsin inhibitors. On the basis of knowing its physical and chemical properties, its activity may also be eliminated, promoting the development and utilization of mulberry leaf resources in animal feed, providing new perspectives and ideas for the development and utilization of mulberry leaves in animal feed and health food, and improving economic benefits of mulberry resources.

DETAILED DESCRIPTION OF EMBODIMENTS

Figure 1:
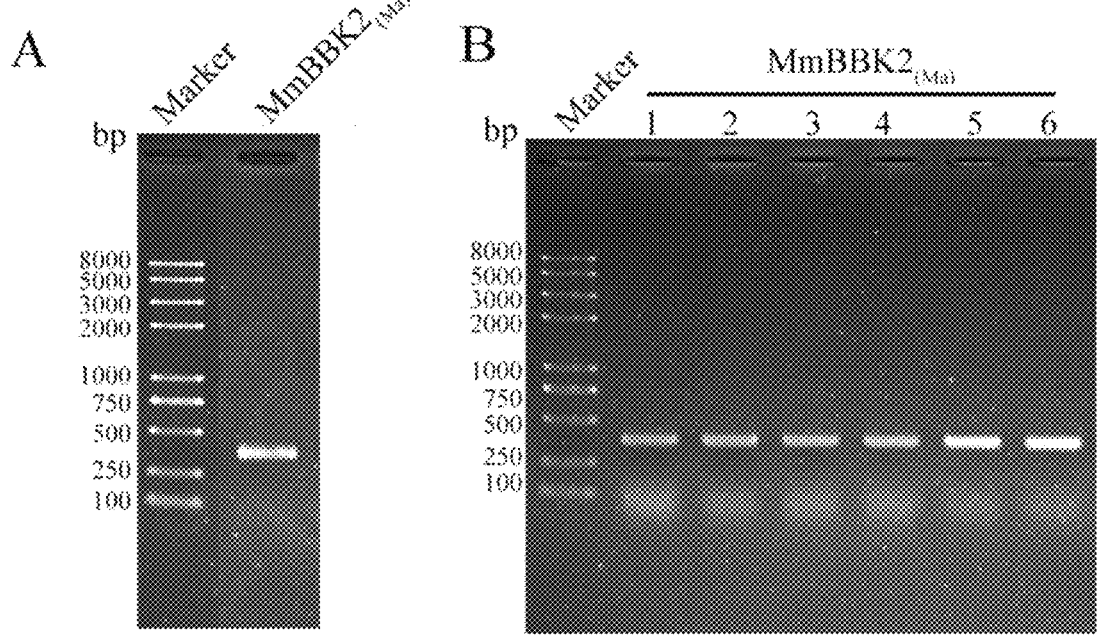
FIG. 1 shows the electrophoresis detection of PCR (Polymerase Chain Reaction) amplification product of MmBBK2$_{(Ma)}$ in (A), and the PCR detection of the bacterial liquid in (B).

The present disclosure will be described in detail below with reference to the accompanying drawings and specific embodiments, but it should not be understood as limitations of the present disclosure. Unless otherwise specified, the technical solutions used in the following embodiments or examples are optional. The materials, reagents, etc. used in the following embodiments or examples can all be obtained from commercial sources, unless otherwise specified.

The following embodiments involve p28 expression vectors deposited by the Institute of Vitamin D Physiology and Applications, Shaanxi University of Technology.

Embodiment I

1 Experimental Method 1.1 RNA Extraction from "Jin 10" Leaves and Synthesis of First-Strand of cDNA 1.1.1 Extraction of Mulberry Leaves RNA Uses Eastep Super Total RNA Extraction Kit (Promega Company), the Extraction is Operated According to the Instructions.

1.1.2 Synthesis of the First Strand of cDNA

Denature and melt the total RNA. Take 4 µg of total RNA, add 1 µL of Oligo(dT), and make up to 10 µL with RNase-free water. Place them in the PCR amplifier at 42° C. for 30 min, and then at 85° C. for 5 s. After the reaction is completed, quickly take them out and place them in ice, dilute them 2.5 times and store them at −20° C.

RT-PCR Reaction System:

| | |
|---|---|
| 2 × ES | 10 µL |
| RNase-free water | 3.4 µL |
| Oligo(dT) | 1 µL |
| gDNA Remover | 1 µL |
| Easy mix | 1 µL |
| RNA | 3.6 µL |

1.2 Construction of Expression Vector 1.2.1 PCR Amplification of Target Fragments of Inhibitors in Mulberry Leaves Based on the CDS sequence of protease inhibitors in *Morus alba*, primers were designed for the MmBBK2 gene (the names were designed and named by the applicant's team). The primer sequences are shown in Table 1.

TABLE 1

Primers used for TA cloning of protease inhibitor MmBBK2

| Primers | Sequence of primers (5' to 3') | SEQ ID NO. |
|---|---|---|
| MmBBK2 (Ma)-TA-F | ATGGCATTCATCAAAGTTTCTGT | 5 |
| MmBBK2 (Ma)-TA-R | TCATGCGCCTTTGACAGC | 6 |

Note:
The subscript "Ma" indicates the primers designed based on the database of *Morus alba*.

Use Jin 10 leaf cDNA as a template for PCR amplification. The PCR system is as follows:

| | |
|---|---|
| Forward Primer | 0.5 µL |
| Reverse Primer | 0.5 µL |
| 10 × Ex Taq buffer | 2.5 µL |
| 2.5 mM dNTPs | 2 µL |
| ddH₂O | 18.375 µL |
| cDNA | 1 µL |
| Takara Ex Taq | 0.125 µL |
| Total | 25 µL |

PCR amplification program: pre-denaturation at 94° C. for 5 min; 30 cycles of denaturation at 94° C. for 30 s, annealing at 53° C. for 30 s, and extension at 72° C. for 1 min or 75 s; and extension at 72° C. for 10 min. The PCR products were separated by 1.5% agarose gel electrophoresis and purified with reference to the EasyPure PCR Purification Kit. Refer to the instruction manual of pEASY-T1 Simple Cloning Vector to ligate the recovered target fragment into the pEASY-T1 Simple vector. The reaction system is: add 4 µL of the target fragment to 1 µL of pEASY-T1 Simple vector, mix and centrifuge briefly, and ligate in a PCR amplifier at 25° C. for 10 min. The ligation product was transformed into *Escherichia coli* DH5α competent cells, and large and round white single colonies were selected for shaking. Positive clones were screened through bacterial liquid PCR, verified by sequencing, and plasmids were extracted.

The plasmid obtained by TA cloning (diluted 20 times) was used as a template for PCR amplification. The primer sequences are shown in Table 2.

TABLE 2

Primers used in construction of protease inhibitor MmBBK2-X1 and MmBBK2-X2 expression vectors

| Primers | Sequence of primers (5' to 3') | SEQ ID NO. |
|---|---|---|
| MmBBK2.X1-p28-F | CGCCATATGCGGGGAAACCTTTTCCGG | 7 |
| MmBBK2-X2-p28-F | CGCATTAATCGGGGAAACCTTTTCCGG | 8 |
| MmBBK2-X1/X2-p28-R | ATTTGCGGCCGCTCATGCGCCTTTGACAGCG | 9 |

Note:
The underline indicates the restriction enzyme cutting site. Nde I site: CATATG; Ase I site: ATTAAT; Not I site: GCGGCCGC. The subscript "Ma" indicates the primers designed based on the *Morus alba* database.

The PCR system is as follows:

| Forward Primer | 0.5 μL |
|---|---|
| Reverse Primer | 0.5 μL |
| 5 × FastPfu Fly buffer | 5 μL |
| 2.5 mM dNTPs | 2 μL |
| ddH₂O | 9.5 μL |
| cDNA | 1 μL |
| 50 mM MgSO₄ | 1 μL |
| 5 × PCR stimulant | 5 μL |
| FastPfu Fly DNA Polymerase | 0.5 μL |
| Total | 25 μL |

PCR amplification program: pre-denaturation at 95° C. for 2 min; 30 cycles denaturation at 95° C. for 30 s, annealing at 61° C. for 30 s, and extension at 72° C. for 30 s; and extension at 72° C. for 10 min. The PCR product was separated by 1.5% agarose gel electrophoresis, and it was gel-extracted, recovered and purified with reference to the EasyPure Quick Gel Extraction Kit. The PCR product and the p28 vector were double-enzyme digested. The double-enzyme digestion reaction system is shown in Table 3. Enzyme digestion conditions: 37° C. for 12 hours, add 10× Loading buffer to terminate enzyme digestion. The digested product was separated by 1.5% agarose gel electrophoresis, and it was gel-extracted and recovered with reference to the EasyPure Quick Gel Extraction Kit.

TABLE 3

Double enzyme digestion reaction system

| Reagents | PCR product double-enzyme digestion system | p28 vector double-enzyme digestion system |
|---|---|---|
| PCR product | 25 μL | |
| p28 plasmid | | 20 μL |
| 10 × H buffer | 5 μL | 5 μL |
| BSA(0.1%) | 5 μL | 5 μL |
| Nde I or Ase I | 2 μL | 2.5 μL |

TABLE 3-continued

Double enzyme digestion reaction system

| Reagents | PCR product double-enzyme digestion system | p28 vector double-enzyme digestion system |
|---|---|---|
| Not I | 2 μL | 2.5 μL |
| ddH₂O | 11 μL | 15 μL |
| Total volume | 50 μL | 50 μL |

After digestion at 37° C. overnight, add 10× Loading buffer to terminate digestion. The digested products were separated by 1.5% agarose gel electrophoresis and gel-extracted with reference to the EasyPure Quick Gel Extraction Kit.

1.2.2 Ligate the Target Fragment to the p28 Vector

Ligate the target fragment to the p28 vector at 16° C. for 2 hours. The ligation system is as follows:

| Target fragment | 1 μL |
|---|---|
| p28 vector | 6 μL |
| T4 DNA ligase buffer | 2 μL |
| T4 DNA ligase | 1 μL |

1.2.3 Transformation

Transform the ligation product into *Escherichia coli* DH5α competent cells. The specific transformation steps are as follows:

1) Place the DH5α competent cells on ice. When they have just melted, add the ligation product, mix gently by pipetting, and let stand on ice for 30 minutes.

2) Heat shock at 42° C. for 90 seconds, then quickly place them on ice and let stand for 5 minutes.

3) Add 900 μL of 2-YT liquid medium without antibiotics and incubate at 37° C. and 220 rpm for 1 hour.

4) Centrifuge at 3500 rpm for 5 minutes, discard 800 μL of the supernatant, resuspend the pellet and supernatant with a pipette, add resuspension liquid to 2-YT solid medium containing kanamycin resistance, and use a sterilized coating stick to lightly coat evenly.

5) Place it upright for 10 minutes in a 37° C. constant-temperature incubator, then invert it for 12 hours.

1.2.4 Bacterial Liquid PCR Screening of Positive Clones and Sequencing

Pick 6 large, round white single colonies, inoculate them into 600 µL of 2-YT liquid medium containing kanamycin resistance, and culture them with shaking at 37° C. and 220 rpm for 4 hours. Take 2 µL of bacterial liquid as a template for bacterial liquid PCR. The bacterial liquid PCR reaction system is as follows:

| | |
|---|---|
| Forward Primer | 0.5 µL |
| Reverse Primer | 0.5 µL |
| 2 × Fine Taq mix | 12.5 µL |
| Bacterial liquid | 2 µL |

The PCR program was: pre-denaturation at 95° C. for 5 min; 30 cycles of denaturation at 95° C. for 30 s, annealing at 61° C. for 30 s, and extension at 72° C. for 1 min; and extension at 72° C. for 10 min. The PCR product was tested by 1.5% agarose gel, and the bacterial liquid that could amplify the target band was a positive clone. Select three positive clones with bright bands, take 200 µL of each and send them to Sangon Biotech (Shanghai, China) for sequencing.

1.2.5 Preparation of Glycerol Bacteria and Plasmid Extraction

According to the ratio of 1/100~1/1000, take the correctly sequenced bacterial liquid and put it into the 2-YT liquid medium containing kanamycin resistance, shake-culture at 37° C. and 220 rpm for 12 hours; take 300 µL of bacterial liquid and mix with 200 µL of 50% glycerol to prepare glycerol bacteria and store it at –20° C. Pipette 2 mL of bacterial liquid and extract the plasmid with reference to the EasyPure Plasmid MiniPrep Kit.

1.3 Prokaryotic Expression of MmBBK2-X1 and MmBBK2-X2

1.3.1 Transform into *Escherichia coli* Expression Strain

Transform the plasmid into *Escherichia coli* BL21(DE3) and Origami 2(DE3) strains. The transformation steps are as follows:

1) Place the BL21(DE3) or Origami 2(DE3) competent cells stored at –80° C. on ice. When they have just melted, take 1 µL of plasmid and slowly add it to the competent cells and mix gently, bath for 30 minutes.

2) Heat shock at 42° C. for 90 seconds. After the heat shock is completed, quickly insert it into ice and cool it for 5 minutes.

3) Add 900 µL of 2-YT liquid medium without antibiotics and incubate at 37° C. and 220 rpm for 1 hour.

4) Centrifuge at 3500 rpm for 5 minutes and discard 800 µL of supernatant.

5) Mix the remaining supernatant and pellet with a pipette, and place the suspension in a 2-YT solid medium containing one antibiotic (kanamycin resistance) or three antibiotics (kanamycin, streptomycin, and tetracycline), use a sterilized coating stick to gently spread evenly.

6) Place the solid plate upright in a 37° C. incubator for 10 minutes, then invert it for 12 hours.

1.3.2 Induced Expression

1) Pick large and round single colonies and culture them in 600 µL of 2-YT liquid culture medium containing one antibiotic (kanamycin resistance) or three antibiotics (kanamycin, streptomycin, tetracycline), incubate overnight at 37° C. and 220 rpm on a constant temperature shaker.

2) Take 150 µL of bacterial liquid that was shaken overnight in 15 mL of 2-YT liquid culture medium with the corresponding antibiotics, and culture it at 37° C. and 220 rpm until the bacterial liquid $OD_{600}$=0.6~1.0, then quickly insert it into ice to slow down growth.

3) Add 0.1 M IPTG stock solution (i.e. working concentration is 0.2 mM) at a ratio of 1/500, and induce at 37° C. and 220 rpm for 5 h or 16° C. and 220 rpm for 20 h.

4) After induction, centrifuge at 4° C. and 6000 rpm for 20 minutes and discard the supernatant.

5) Add 1.5 mL of 1× binding buffer to resuspend the bacterial cells, centrifuge at 4° C. and 6000 rpm for 10 min, and discard the supernatant.

6) Add 1 mL of 1× binding buffer to resuspend the bacterial cells, centrifuge again, and discard the supernatant.

7) Finally add 450 µL of 1× binding buffer to resuspend the bacterial cells and store at –20° C.

1.3.3 Cell Disruption

Place the bacterial cell mixture in the ice-water mixture, use a 30 W ultrasonic disruptor to crush the bacterial cell mixture until the bacterial cell mixture is translucent, centrifuge at 4° C. and 16000 g for 30 minutes, separate the supernatant, and add 250 µL of 1× binding buffer to the sediment for resuspending to obtain an inclusion body solution, and store the supernatant and precipitate at –20° C.

1.4 SDS-PAGE and Native PAGE, and Activity Staining of MmBBK2-X1 and MmBBK2-X2

1.5 Effects of Different pH, High Temperature and High Pressure, Reducing Agent and Maillard Reaction on the Activity of MmBBK2-X2

2 Results and Analysis 2.1 Construction of MmBBK2$_{(Ma)}$ Expression Vector

Figure 2:
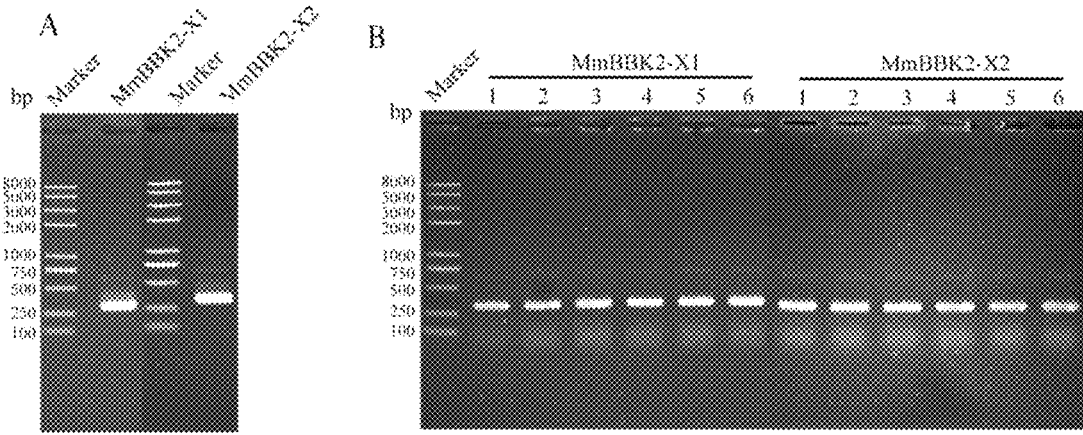
FIG. 2 shows the electrophoresis detection of PCR amplification products of MmBBK2-X1 and MmBBK2-X2 in (A), and the PCR detection of the bacterial liquid in (B).

The PCR product detection results showed that the target gene band amplified by PCR was single and bright. The PCR product was ligated to the T vector and transferred into DH5α competent cells. The bacterial liquid was taken for bacterial liquid PCR. The PCR product of the bacterial liquid was tested with 1.0% agarose gel. The results showed that all MmBBK2$_{(Ma)}$ were positive clones (FIG. 1). Sequencing of bacterial liquid revealed that MmBBK2$_{(Ma)}$ exists in two forms. We named the two forms of MmBBK2 successfully cloned as: MmBBK2-X1 and MmBBK2-X2 respectively. Next, we extracted the plasmid and performed subcloning. MmBBK2-X1 and MmBBK2-X2 were amplified by PCR to obtain bright and single bands. Afterwards, the PCR product was connected/ligated to the p28 vector and transferred into DH5α competent cells, the bacterial liquid PCR was performed, and 1% agarose gel electrophoresis was used for detection. The results are shown in FIG. 2. The bacterial liquid of positive clones was selected, and sequencing confirmed that the MmBBK2-X1-p28 and MmBBK2-X2-p28 expression vectors were successfully constructed.

2.2 Primary Structure Analysis of MmBBK2-X1 and MmBBK2-X2

Figure 3:
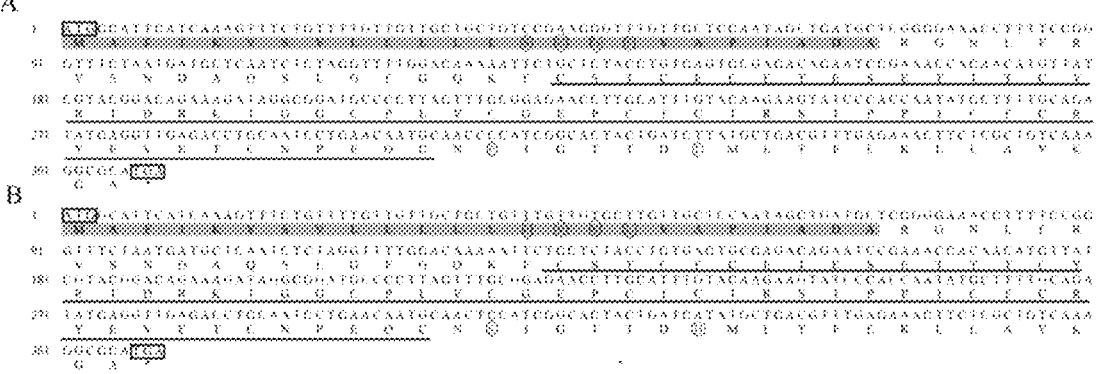
FIG. 3 shows the nucleotide sequences of MmBBK2-X1 (A) and MmBBK2-X2 (B) and their derived amino acid sequences. The gray background part is the signal peptide sequence, the underlined part is the BowB domain, the hexagonal box indicates differential amino acids between different subtypes of the same protease inhibitor. The start codon (ATG) and stop codon (TAA) are shown in the boxes.

The CDS coding frames of MmBBK2-X1 and MmBBK2-X2 both consist of 369 nucleotides, encoding a protein of 122 amino acids. Both have 12 cysteine residues in their amino acid sequences, and 6 amino acid substitutions in their amino acid sequences, but the amino acid properties are similar. The MmBBK2-X1 gene sequence is shown in SEQ ID NO. 1, and the amino acid sequence of its encoded protein is shown in SEQ ID NO. 3; the MmBBK2-X2 gene sequence is shown in SEQ ID NO. 2, and the amino acid sequence of its encoded protein is shown in SEQ ID NO. 4. Both MmBBK2-X1 and MmBBK2-X2 proteins have a signal peptide consisting of 24 amino acids (FIG. 3). The molecular weights of the mature form of the protein are 10801.38 Da and 10815.33 Da. The isoelectric points (pI) are 5.08 and 5.34 respectively. Both have a BowB domain containing 12 cysteine residues.

2.3 Prokaryotic Expression of MmBBK2-X1 and MmBBK2-X2

Figure 4:
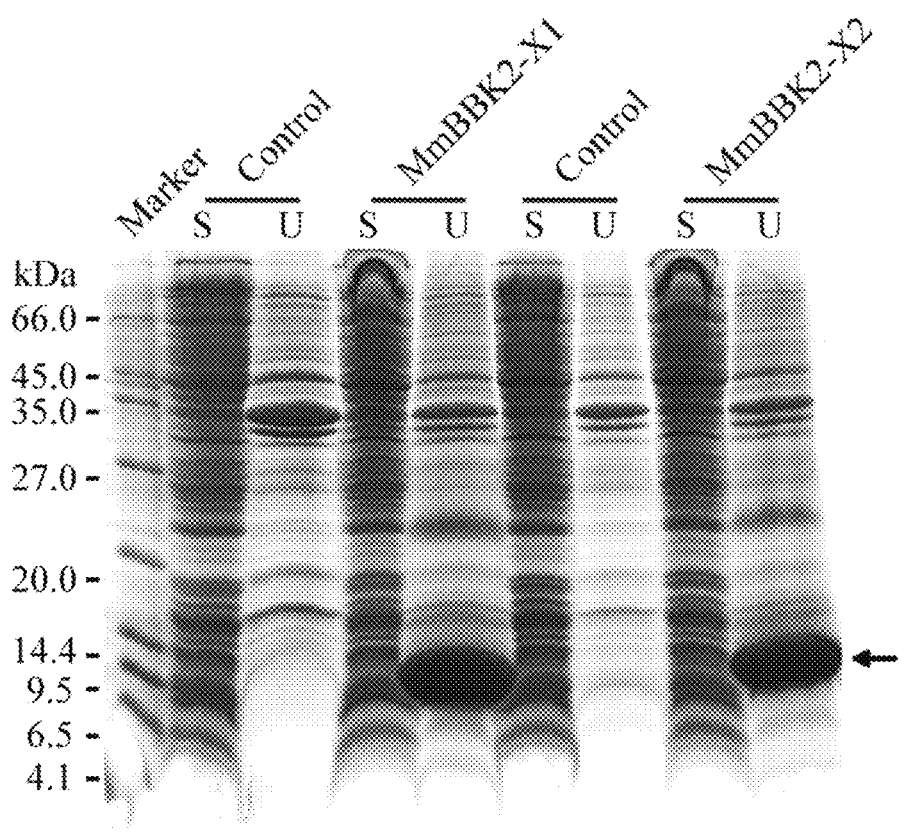
FIG. 4 shows SDS-PAGE analysis of MmBBK2-X1 and MmBBK2-X2 expressed in BL21(DE3) cells. "S" indicates soluble protein; "U" indicates unsoluble protein; "Control", cell lysate of BL21(DE3) strain transformed into p28 empty vector.
Figure 5:
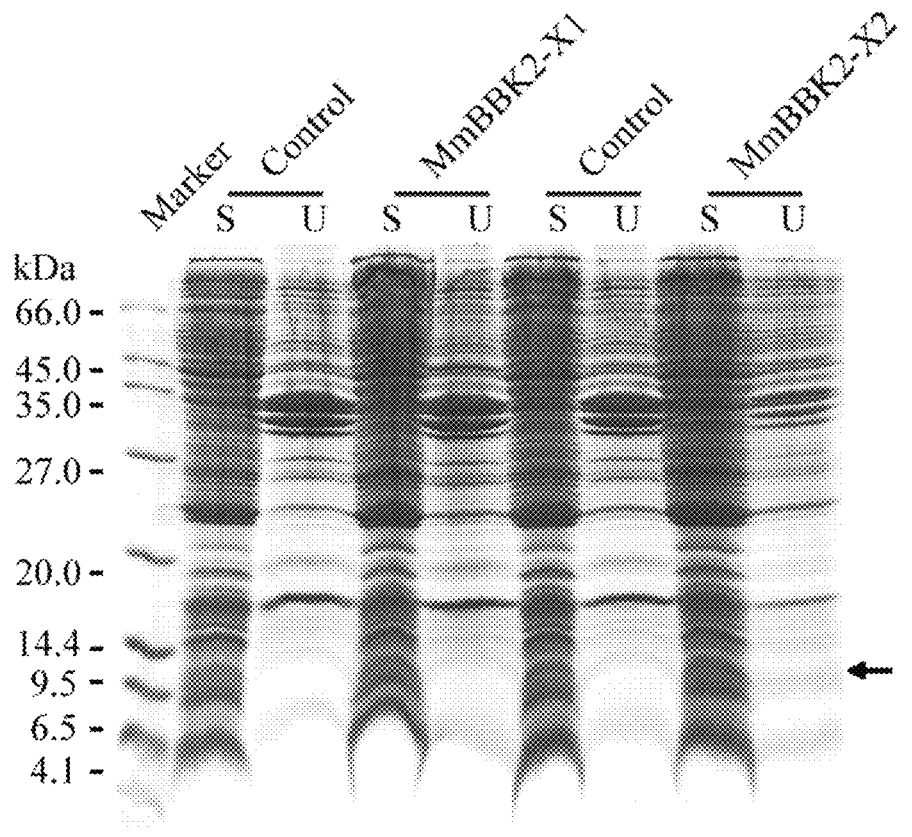
FIG. 5 shows SDS-PAGE analysis of MmBBK2-X1 and MmBBK2-X2 expressed in Origami 2(DE3) cells. "S" indicates soluble protein; "U" indicates unsoluble protein; "Control", cell lysate of Origami 2(DE3) strain transformed into p28 empty vector.

In order to achieve prokaryotic expression of MmBBK2-X1 and MmBBK2-X2, the recombinant plasmids were transferred into two expression strains of *Escherichia coli* BL21(DE3) (FIG. 4) and Origami 2(DE3) (FIG. 5), and IPTG with a working concentration of 0.2 mM was used to induce expression. The target protein was separated and detected using 16.5% SDS-PAGE. The results showed that when the IPTG concentration was 0.2 mM, MmBBK2-X1 and MmBBK2-X2 were mainly expressed in soluble form in Origami 2(DE3) strain, and they mainly exist in the form of inclusion bodies in BL21(DE3) strains.

2.4 Activity Analysis of MmBBK2-X1 and MmBBK2-X2

Figure 6:
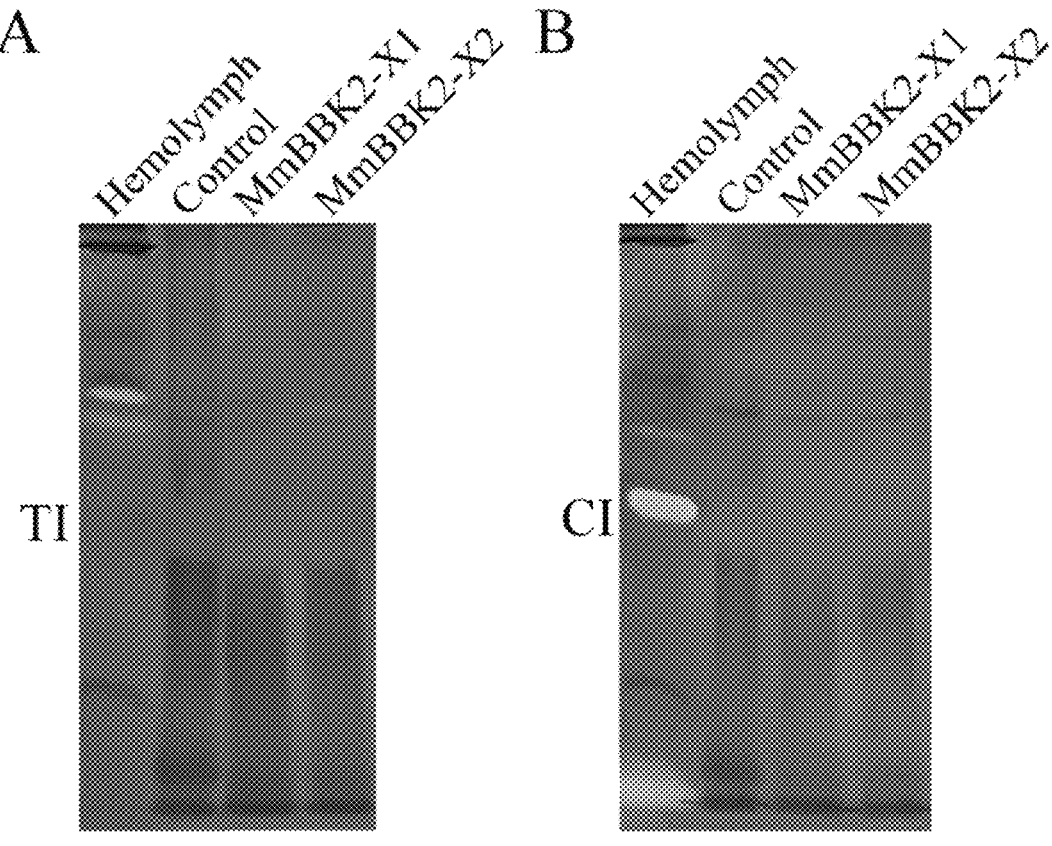
FIG. 6 shows the TI (A) and CI (B) activity analysis of MmBBK2-X1 and MmBBK2-X2 expressed in BL21(DE3) cells. "TI" and "CI" stand for trypsin inhibitor and chymotrypsin inhibitor, respectively. *Bombyx mori* hemolymph from day-5 fifth-instar larvae was used as a positive control. "Control", cell lysate of BL21(DE3) strain transformed into p28 empty vector. Arrows indicate protease inhibitor activity bands.
Figure 7:
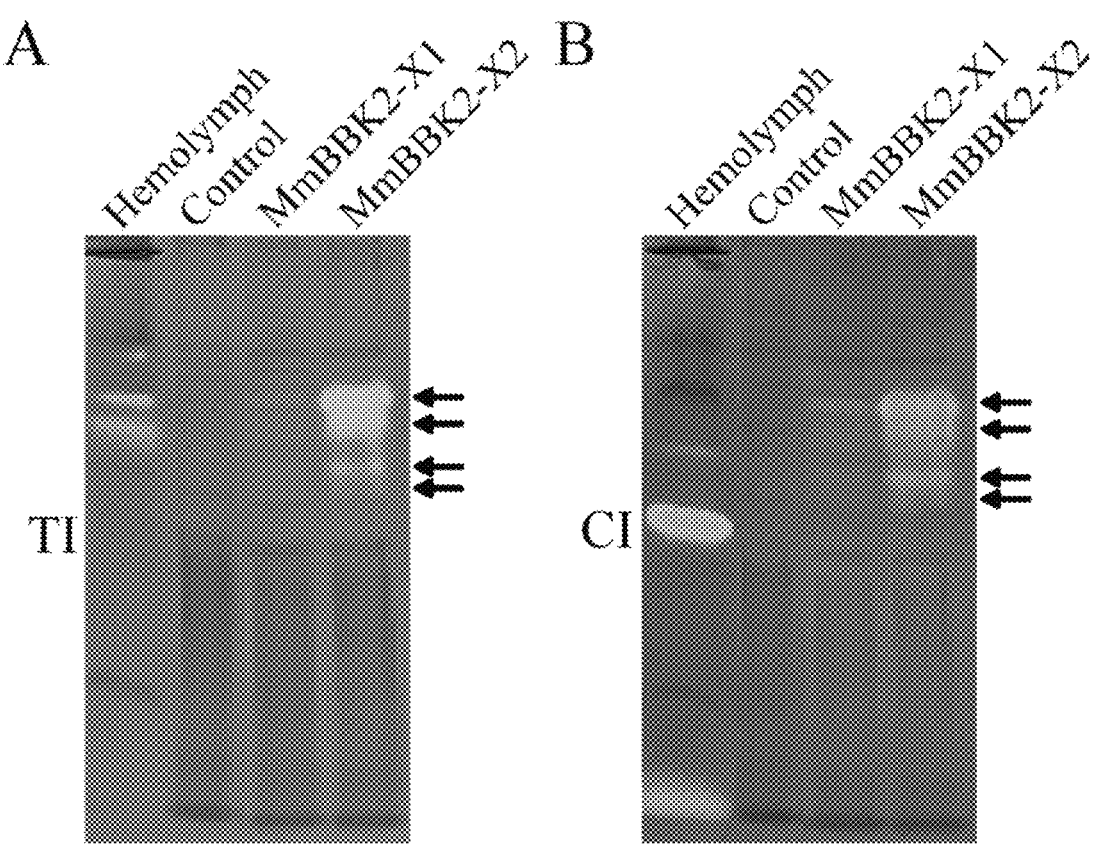
FIG. 7 shows the TI (A) and CI (B) activity analysis of MmBBK2-X1 and MmBBK2-X2 expressed in Origami 2(DE3) cells. "TI" and "CI" stand for trypsin inhibitor and chymotrypsin inhibitor, respectively. *Bombyx mori* hemolymph from day-5 fifth-instar larvae was used as a positive control. "Control", cell lysate of Origami 2(DE3) strain transformed into p28 empty vector. Arrows indicate protease inhibitor activity bands.

In order to analyze the inhibitory activity of the target protein against trypsin and chymotrypsin, we separated the supernatants of the target protein expressed in the two strains (BL21(DE3) and Origami 2(DE3)) by 10% Native PAGE, and then performed in-gel activity staining. No trypsin or chymotrypsin inhibitor activity of MmBBK2-X1 and MmBBK2-X2 was detected in the BL21(DE3) strain (FIG. 6); in the Origami 2(DE3) strain, MmBBK2-X1 and MmBBK2-X2 has inhibitory activity against both trypsin and chymotrypsin (FIG. 7).

2.5 Effects of pH, Temperature, Reducing Agent and Maillard Reaction on the Activity of MmBBK2-X2

(1) Effect of Different pH on MmBBK2-X2 Activity

Figure 8:
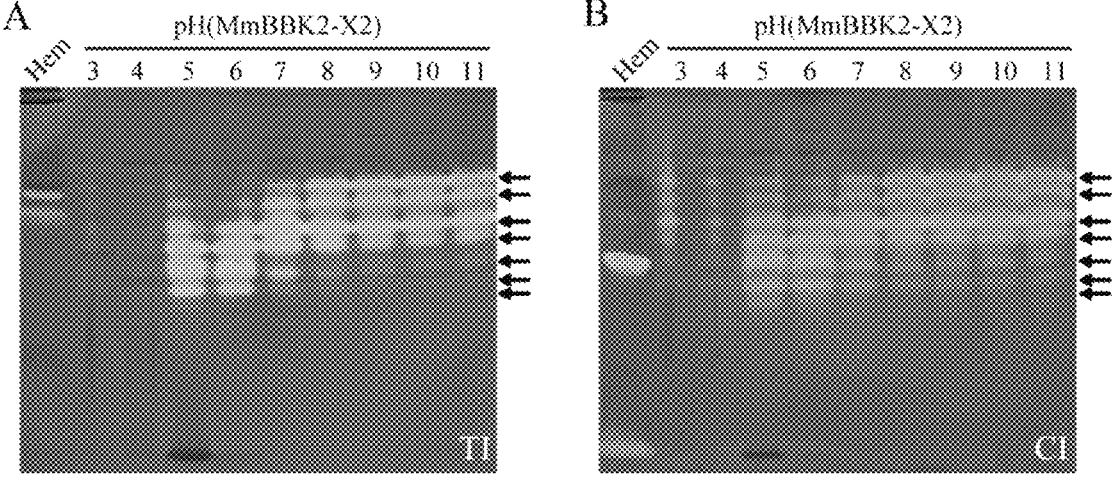
FIG. 8 shows the effect of different pH on the activity of MmBBK2-X2.

As shown in FIG. 8, MmBBK2-X2 is more stable in an alkaline environment than in an acidic environment. In the pH range of 5~6, MmBBK2-X2 shows the strongest inhibitory activity, and compared with the pH range of (7~11), the position of the active band changed, and the inhibitory activity of MmBBK2-X2 was basically lost within the pH range of 3~4.

(2) Effect of High Temperature and High Pressure on MmBBK2-X2 Activity

Figure 9:
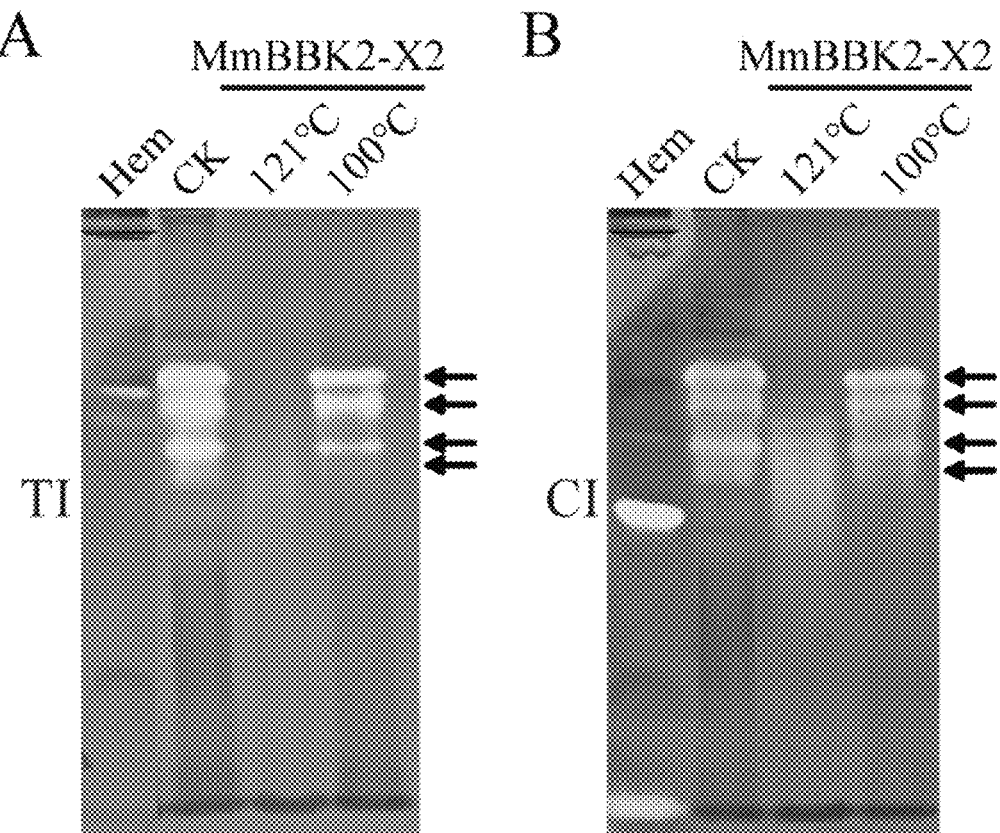
FIG. 9 shows the effect of high temperature and high pressure on the activity of MmBBK2-X2.

In order to verify the effect of high temperature or combination of high temperature and high pressure on the activity of protease inhibitor MmBBK2-X2, we treated the protease inhibitor at 121° C. and 0.21 MPa or 100° C. for 20 min, and then analyzed its inhibitory activity against protease by Native PAGE and in-gel activity staining. In-gel activity staining results showed (FIG. 9) that compared with the control group, treatment at 100° C. for 20 minutes slightly reduced the inhibitory activity of MmBBK2-X2 against trypsin and chymotrypsin, while the combination of high temperature and high pressure (121° C. and 0.21 MPa)

would greatly weaken the inhibitory activity of MmBBK2-X2 against trypsin and chymotrypsin.

(3) Effect of Reducing Agent on MmBBK2-X2 Activity

Figure 10:
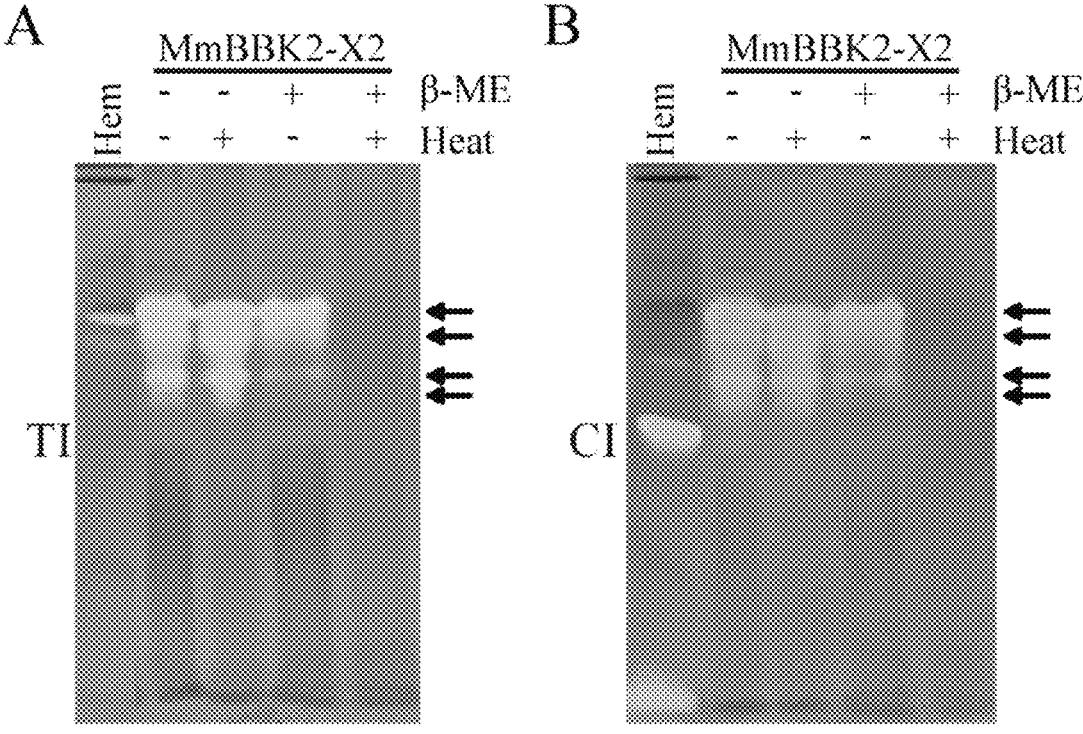
FIG. 10 shows the effect of β-mercaptoethanol on the activity of MmBBK2-X2.

In order to explore the effect of reducing agents on the activity of MmBBK2-X2, we used β-mercaptoethanol to treat the protease inhibitor MmBBK2-X2 and analyzed its inhibitory activity against trypsin and chymotrypsin. The results are shown in FIG. 10. In the absence of β-mercaptoethanol, heating has no significant effect on the activity of protease inhibitors; in the presence of β-mercaptoethanol without heating, the inhibitory activity of MmBBK2-X2 against proteases is reduced to a certain extent; in the presence of β-mercaptoethanol and heating, the inhibitory activity of MmBBK2-X2 against proteases is completely lost. This shows that there is a disulfide bridge in the MmBBK2-X2 structure, and the disulfide bridge is an important structure to maintain its activity.

(4) Effect of Glucose-Mediated Maillard Reaction on MmPI Activity

Figure 11:
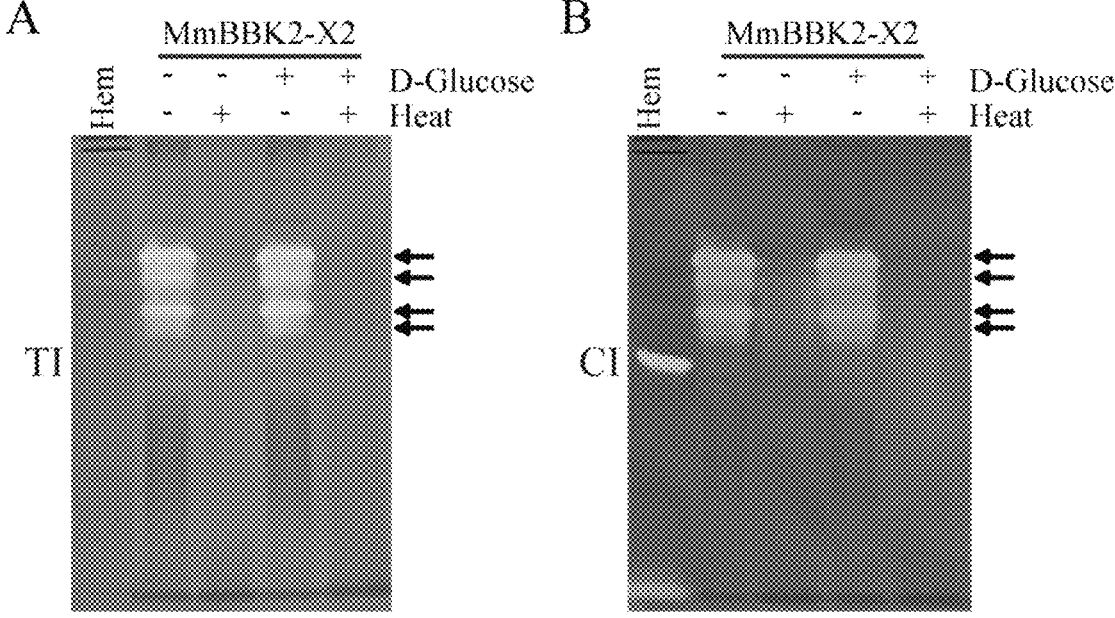
FIG. 11 shows the effect of Maillard reaction on the activity of MmBBK2-X2.

As shown in FIG. 11, in the absence of glucose, heating at 100° C. for 60 minutes greatly weakened the inhibitory activity of MmBBK2-X2 against trypsin and chymotrypsin; in the presence of glucose without heating, MmBBK2-X2 had no significant effect on the inhibitory activity against proteases. MmBBK2-X2 is completely inactivated in the presence of glucose and heating. The above results indicate that the Maillard reaction mediated by glucose can completely eliminate the inhibitory activity of MmBBK2-X2 against trypsin and chymotrypsin.

Although the preferred embodiments of the present disclosure have been described, additional changes and modifications to these embodiments may be made by those skilled in the art once the basic inventive concepts are apparent. Therefore, it is intended that the appended claims should be construed to include the preferred embodiments and all changes and modifications that fall within the scope of the present disclosure.

Obviously, various changes and modifications to the present disclosure may be made by those skilled in the art without departing from the spirit and scope of the present disclosure. Thus, if these changes and modifications of the present disclosure fall within the scope of the claims of the present disclosure and equivalent technologies thereof, the present disclosure is also intended to include these modifications and variations.

CROSS-REFERENCE TO SEQUENCE LISTING XML FILE

This application contains a Sequence Listing XML as a separate part of the disclosure, which presents nucleotide and/or amino acid sequences and associated information using the symbols and format in accordance with the requirements of 37 CFR-1.831-1.835. The XML file named "MmBBK2 Sequence File v2.xml", created Dec. 10, 2023, 9,672 bytes in size, is submitted herewith and is incorporated by reference in its entirety.

---

---

What is claimed is:

1. A method of preparing a trypsin and chymotrypsin inhibitor composition, comprising adding an effective amount of MmBBK2 protein, comprising the amino acid sequence of SEQ ID NO: 1 or SEQ ID NO: 2, to a composition comprising a protease inhibitor; and wherein SEQ ID NO: 1 is encoded by a gene comprising the nucleotide sequence of SEQ ID NO: 3, and SEQ ID NO: 2 is encoded by a gene comprising the nucleotide sequence of SEQ ID NO: 4.

2. A plasmid, comprising:

the nucleotide sequence of SEQ ID NO: 3 inserted between the Nde I and Not I restriction sites; or the nucleotide sequence of SEQ ID NO: 4 inserted between the Ase I and Not I restriction sites.

3. A host strain transformed with the plasmid of claim 2, wherein the host strain is *Escherichia coli*.

4. A method of eliminating trypsin and chymotrypsin inhibitory activity of the MmBBK2 protein of claim 1, comprising:

1) Subjecting the MmBBK2 protein to a pH of 3-4;

2) incubating the MmBBK2 protein at a temperature of 121° C. and a pressure of 0.21 MPa for 20 minutes;

3) incubating the MmBBK2 protein with β-mercaptoethanol at a temperature of 100° C. for 10 minutes; or 4) performing a Maillard reaction on the MmBBK2 protein in the presence of glucose.

\* \* \* \* \*